United States Patent
Kumar et al.

(10) Patent No.: US 6,211,351 B1
(45) Date of Patent: Apr. 3, 2001

(54) CHIMERIC MUTATIONAL VECTORS

(75) Inventors: Ramesh Kumar, Pennington; Richard A. Metz, Lawrenceville, both of NJ (US)

(73) Assignee: ValiGen (US), Inc., Newtown, PA (US)

( * ) Notice: Subject to any disclaimer, the term of this patent is extended or adjusted under 35 U.S.C. 154(b) by 0 days.

(21) Appl. No.: 09/429,292

(22) Filed: Oct. 28, 1999

Related U.S. Application Data

(63) Continuation of application No. 09/078,063, filed on May 12, 1998, now Pat. No. 6,004,804.

(51) Int. Cl.[7] ............ C12N 15/11; C12N 15/00; C12N 15/09; C07H 21/04

(52) U.S. Cl. ............ 536/23.1; 536/24.2; 435/6; 435/69.1; 435/91.1; 435/320.1; 435/440; 435/455; 435/462; 435/463

(58) Field of Search ............ 435/6, 69.1, 91.1, 435/440, 455, 462, 463, 320.1; 536/23.1, 24.3, 24.31, 24.32, 24.2

(56) References Cited

U.S. PATENT DOCUMENTS

| | | | |
|---|---|---|---|
| 5,565,350 | 10/1996 | Kmiec | 435/463 |
| 5,731,181 | 3/1998 | Kmiec | 435/6 |
| 5,760,012 | 6/1998 | Kmiec et al. | 514/144 |
| 5,872,232 | 2/1999 | Cook et al. | 536/23.1 |
| 5,948,653 * | 9/1999 | Pati et al. | 435/6 |
| 6,004,804 | 12/1999 | Kumar et al. | 435/320.1 |

FOREIGN PATENT DOCUMENTS

WO 97/26334 7/1997 (WO).

OTHER PUBLICATIONS

Kotani, H. et al. Mol. Gen. Genet. (1996) vol. 250:626–634.*
Yoon, K. et al. Proc. Natl. Acad. Sci. USA, vol. 93, pp. 2071–2076 (Mar. 1996).*
Cole–Strauss, A. et al. Science vol. 273, 1386–1389 (Sep. 1996).*
Wang, S. et al. Nucleic Acids Research, vol. 23, No. 7, pp. 1157–1164 (1995).*
Campbell et al., 1989, "Homologous recombination involving small single–stranded oligonucleotides in human cells", The New Biologist 1:223–227.
Cole–Strauss et al., 1996, "Correction of the mutation responsible for sickle cell anemia by an RNA–DNA oligonucleotide", Science 273(5280):1386–9.
Durand et al., 1990, "Circular dichroism studies of an oligodeoxyribonucleotide containing a hairpin loop made of a hexaethylene glycol chain: conformation and stability", Nucleic Acids Res. 18(21):6353–9.

(List continued on next page.)

Primary Examiner—Robert A. Schwartzman
Assistant Examiner—Mark L. Shibuya
(74) Attorney, Agent, or Firm—Pennie & Edmonds LLP

(57) ABSTRACT

The invention is based on the discovery that recombinagenic oligonucleobases are active in prokaryotic cells that contain a strand transfer activity (RecA) and mismatch repair activity (MutS). Using this system a type of Duplex Mutational Vector termed a Heteroduplex Mutational Vector, was shown to be more active in prokaryotic cells than the types of mutational vectors heretofore tested. Further improvements in activity were obtained by replacing the tetrathymidine linker by a nuclease resistant oligonucleotide, such as tetra-2'-O-methyl-uridine, to link the two strands of the recombinagenic oligonucleobase and removing the DNA-containing intervening segment. The claims concern Duplex Mutational Vectors that contain the above improvements. In an alternative embodiment the claims concern the use of Duplex Mutational Vectors in prokaryotic cells.

25 Claims, 1 Drawing Sheet

Double Hairpin

OTHER PUBLICATIONS

Figure 1:
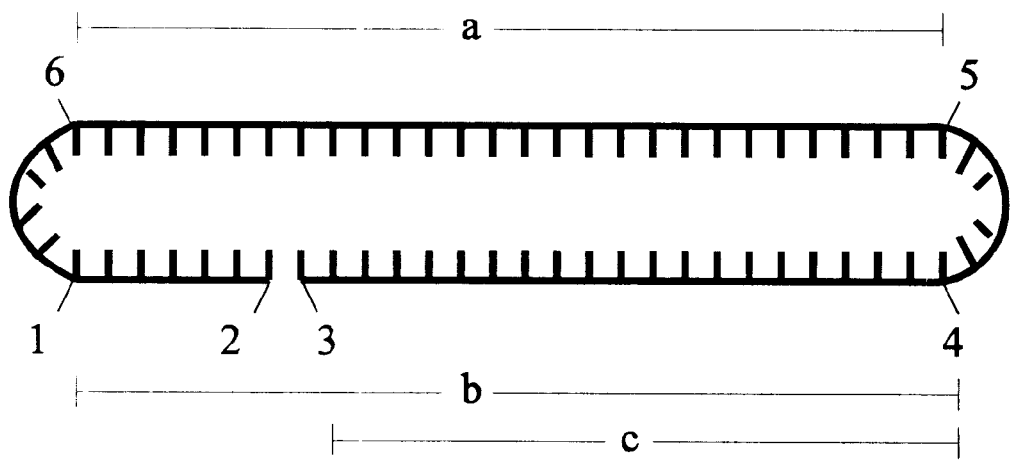

Gamper et al., 1993, "Facile preparation of nuclease resistant 3'modified oligodeoxynucleotides", Nucleic Acids Res. 21(1):145–50.

Hosoda et al., 1990, "An F factor based cloning system for large DNA fragments", Nucleic Acids Res. 18(13):3863–9.

Hunger–Bertling et al., 1990, "Short DNA fragments induce site specific recombination in mammalian cells", Mol Cell Biochem. 92(2):107–16.

Ioannou et al., 1994 "A new bacteriophage P1–derived vector for the propagation of large human DNA fragments", Nat. Gen. 6:85–89.

Kotani et al., 1996, "RNA facilitates RecA–mediated DNA pairing and strand transfer between molecules bearing limited regions of homology", Mol Gen Genet 250(5):626–34.

Kren et al., "In vivo site–directed mutagenesis of the factor IX gene by chimeric RNA/DNA oligonucleotides", Nat. Med. 4(3):285–90.

Letsinger et al., 1995, "Use of stilbenedicarboxamide bridge in stabilizing, monitoring, and photochemically altering folded conformations of oligonucleotides", J. Am. Chem. Soc. 117;7323–7328.

Messere et al., 1997, "Cloning and mutageneis of a herpesvirus genome as an infectious bacterial artifical chromosome", Proc. Natl Acad Sci U S A 94(26):14759–63.

Shizuya et al., 1992, "Cloning and stable maintenance of 300–kilobase–pair fragments of human DNA in *Escheria coli* using an F–factor–based vector", Proc Natl Acad Sci U S A 89(18):8794–7.

Yamamoto et al., 1992, "Strand–specifity in the transformation of yeast with synthetic oligonucleotides", Genetics 131(4):811–9.

Yamamoto et al., 1992, "Parameters affecting the frequencies of transformation and co–transformation with synthetic oligonucleotides in yeast", Yeast 8(11):935–48.

Yang et al., 1997, "Homologous recombination based modification in *Escherichia coli* and germline transmission in transgenic mice of a bacterial artificial chromosome", Nat Biotechnol 15(9):859–65.

Yoon et al., 1996, "Targeted gene correction of episomal DNA in mammalina cells meditated by a chimeric RNA.DNA oligonucleotide", Proc Natl Acad Sci U S A 93(5):2071–6.

* cited by examiner

Double Hairpin

Single Hairpin With Overhang

US 6,211,351 B1

CHIMERIC MUTATIONAL VECTORS

This is a continuation of application Ser. No. 09/078,063, filed May 12, 1998, now U.S. Pat. No. 6,004,804.

1. FIELD OF THE INVENTION

The invention concerns the use of duplex oligonucleobase compounds (hereafter "duplex mutational vectors") to specifically make alterations in the sequence of a DNA in a cell. In one embodiment the invention concerns compounds and methods of their use to make specific genetic alterations in the genome and in episomes (plasmids) of target prokaryotic cells. In a further embodiment the invention concerns methods of using bacterial cells to develop more efficient duplex mutational vectors. The structure of the duplex mutational vector (DMV) is designed so that genetic exchange between the DMV and the target gene occurs, i.e., a sequence contained in the DMV replaces the sequence of the target gene. In still further embodiments the invention concerns specific generic structures of DMV.

2. BACKGROUND OF THE INVENTION

U.S. Pat. No. 5,565,350, issued Oct. 15, 1996, and U.S. Pat. No. 5,731,181, issued Mar. 24, 1998 by E. B. Kmiec, described Chimeric Mutational Vectors (CMV), i.e., vectors having both DNA-type and RNA-type nucleobases for the introduction of genetic changes in eukaryotic cells. Such CMV were characterized by having at least 3 contiguous base pairs wherein DNA-type and RNA-type nucleobases are Watson-Crick paired with each other to form a hybrid-duplex. A CMV designed to repair a mutation in the gene encoding liver/bone/kidney type alkaline phosphatase was reported in Yoon, K., et al., March 1996, Proc. Natl. Acad. Sci. 93, 2071. The alkaline phosphatase gene was transiently introduced into CHO cells by a plasmid. Six hours later the CMV was introduced. The plasmid was recovered at 24 hours after introduction of the CMV and analyzed. The results showed that approximately 30 to 38% of the alkaline phosphatase genes were repaired by the CMV.

A CMV designed to correct the mutation in the human β-globin gene that causes Sickle Cell Disease and its successful use was described in Cole-Strauss, A., et al., 1996, Science 273:1386. A CMV designed to create a mutation in a rat blood coagulation factor IX gene in the hepatocyte of a rat is disclosed in Kren et al., 1998, Nature Medicine 4, 285–290. An example of a CMV having one base of a first strand that is paired with a non-complementary base of a second strand is shown in Kren et al., June 1997, Hepatology 25, 1462.

U.S. Pat. No. 08/640,517, filed May 1, 1996, by E. B. Kmiec, A. Cole-Strauss and K. Yoon, published as WO97/41141, Nov. 6, 1997, and U.S. Pat. No. 08/906,265, filed Aug. 5, 1997, disclose methods and CMV that are useful in the treatment of genetic diseases of hematopoietic cells, e.g., Sickle Cell Disease, Thalassemia and Gaucher Disease.

The above-cited scientific publications of Yoon, Cole-Straauss and Kren describe CMV having two 2'-O-methyl RNA segments separated by an intervening DNA segment, which were located on the strand opposite the strand having the 5' end nucleotide. U.S. Pat. No. 5,565,350 described a CMV having a single segment of 2'-O-methylated RNA, which was located on the chain having the 5' end nucleotide. An oligonucleotide having complementary deoxyribonucleotides and a continuous segment of unmodified ribonucleotides on the strand opposite the strand having the 5' end nucleotide was described in Kmiec, E. B., et al., 1994, Mol. and Cell. Biol. 14:7163–7172. The sequence of the strand was derived from the bacteriophage M13mp19, The use of single stranded oligonucleotides to introduce specific mutations in yeast are disclosed in Yamamoto, T., et al., 1992, Genetics 131, 811–819. The oligonucleotides were between about 30 and 50 bases. Similar results were reported by Campbell, C. R., et al., 1989, The New Biologist, 1, 223–227. Duplex DNA fragments of about 160 base pairs in length have been reported to introduce specific mutations in cultured mammalian cells. Hunger-Bertling, K., et al., 1990, Molecular and Cellular Biochemistry 92, 107–116.

Applicants are aware of the following provisional applications that contain teaching with regard to uses and delivery systems of recombinagenic oligonucleotides: By Steer et al., Ser. No. 60/045,288 filed Apr. 30, 1997; Ser. No. 60/054,837 filed Aug. 5,1997; Ser. No. 60/064,996, filed Nov. 10, 1997; and by Steer & Roy-Chowdhury et al., Ser. No. 60/074,497, filed Feb. 12, 1998, entitled "Methods of Prophylaxis and Treatment by Alteration of APO B and APO E Genes."

3. BRIEF DESCRIPTION OF THE FIGURES

FIG. 1. An example of the conformation of a double hairpin type recombinagenic oligomer. The features are: a, first strand; b, second strand; c, first chain of the second strand; 1, 5' most nucleobase; 2,3' end nucleobase; 3,5' end nucleobase; 4,3' most nucleobase; 5, first terminal nucleobase; 6, second terminal nucleobase.

Figure 2:
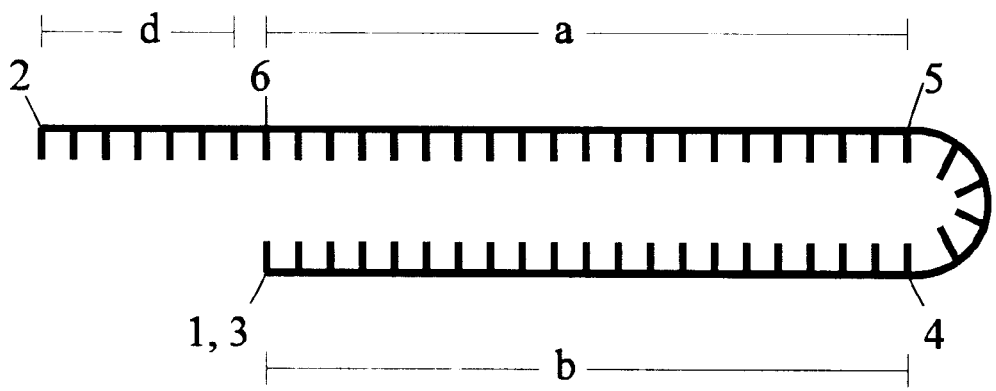

FIG. 2. An example of the conformation of a single hairpin type recombinagenic nucleobase with an overhang. The features are as above with the addition of d, the overhang. Note that the same nucleobase is both the 5' most nucleobase of the second strand and the 5' end nucleobase.

4. DEFINITIONS

The invention is to be understood in accordance with the following definitions.

An oligonucleobase is a polymer of nucleobases, which polymer can hybridize by Watson-Crick base pairing to a DNA having the complementary sequence.

Nucleobases comprise a base, which is a purine, pyrimidine, or a derivative or analog thereof. Nucleobases include peptide nucleobases, the subunits of peptide nucleic acids, and morpholine nucleobases as well as nucleobases that contain a pentosefuranosyl moiety, e.g., an optionally substituted riboside or 2'-deoxyriboside. Nucleotides are pentosefuranosyl containing nucleobases that are linked by phosphodiesters. Other pentosefuranosyl containing nucleobases can be linked by substituted phosphodiesters, e.g., phosphorothioate or triesterified phosphates.

A oligonucleobase compound has a single 5' and 3' end nucleobase, which are the ultimate nucleobases of the polymer. Nucleobases are either deoxyribo-type or ribo-type. Ribo-type nucleobases are pentosefuranosyl containing nucleobases wherein the 2' carbon is a methylene substituted with a hydroxyl, substituted oxygen or a halogen. Deoxyribo-type nucleobases are nucleobases other than ribo-type nucleobases and include all nucleobases that do not contain a pentosefuranosyl moiety, e.g., peptide nucleic acids.

An oligonucleobase strand generically includes regions or segments of oligonucleobase compounds that are hybridized to substantially all of the nucleobases of a complementary strand of equal length. An oligonucleobase strand has a 3' terminal nucleobase and a 5' terminal nucleobase. The 3' terminal nucleobase of a strand hybridizes to the 5' terminal nucleobase of the complementary strand. Two nucleobases of a strand are adjacent nucleobases if they are directly covalently linked or if they hybridize to nucleobases of the complementary strand that are directly covalently linked. An oligonucleobase strand may consist of linked nucleobases, wherein each nucleobase of the strand is covalently linked to the nucleobases adjacent to it. Alternatively a strand may be divided into two chains when two adjacent nucleobases are unlinked. The 5' (or 3') terminal nucleobase of a strand can be linked at its 5'-O (or 3'-O) to a linker, which linker is further linked to a 3' (or 5') terminus of a second oligonucleobase strand, which is complementary to the first strand, whereby the two strands form a single oligonucleobase compound. The linker can be an oligonucleotide, an oligonucleobase or other compound. The 5'-O and the 3'-O of a 5' end and 3' end nucleobase of an oligonucleobase compound can be substituted with a blocking group that protects the oligonucleobase strand. However, for example, closed circular olignucleotides do not contain 3' or 5' end nucleotides. Note that when an oligonucleobase compound contains a divided strand the 3' and 5' end nucleobases are not the terminal nucleobases of a strand.

As used herein the terms 3' and 5' have their usual meaning. The terms "3' most nucleobase", "5' most nucleobase", "first terminal nucleobase" and "second terminal nucleobase" have special definitions. The 3' most and second terminal nucleobase are the 3' terminal nucleobases, as defined above, of complementary strands of a recombinagenic oligoncleobase. Similarly, the 5' most and first terminal nucleobase are 5' terminal nucleobases of complementary strands of a recombinagenic oligonucleobase.

5. SUMMARY OF THE INVENTION

The present invention is based on the unexpected discovery that the Chimeric Mutational Vectors described in the prior art are functional in prokaryotic cells. The invention is further based on the unexpected discovery that the presence of hybrid duplex is not essential for the activity of the mutational vector. Duplex Mutational Vectors that lack three contiguous base pairs of hybrid duplex were unexpectedly found to be effective to introduce specific genetic changes in bacteria. Such vectors are termed Non-Chimeric Mutational Vectors (NCMV). NCMV can also be used in place of CMV in eukaryotic cells.

The present invention is further based on the unexpected finding that a Chimeric Mutational Vector, having a single segment of ribo-type nucleobases located on the strand opposite the strand having the 5' end nucleobase and 3' end nucleobase is superior to the Chimeric Mutational Vectors having two segments of ribo-type nucleobases.

The invention is yet further based on the unexpected discovery of the improved efficiency of a duplex mutational vector wherein the sequence of one strand comprises the sequence of the target gene and the sequence of the second strand comprises the desired sequence, i.e., the different sequence that the user intends to introduce in place of the target sequence. Such duplex vectors are termed Heteroduplex Mutational Vectors (HDMV). An HDMV and can be either Chimeric or Non-Chimeric.

In one embodiment of a HDMV, the strand that comprises the sequence of the different desired sequence is a strand having a 3' end or a 5' end. In an alternative embodiment the strand that comprises the sequence of the different, desired sequence is comprised of no ribo-type nucleobases.

The invention is yet further based on the discovery that significant improvements in the activity can be obtained by constructing the DMV so as to protect the strands of the DMV from the action of 3' exonuclease. In one embodiment 3' exonuclease protection is provided by making the DMV resistant to the action of single strand DNase.

DMV can be used to introduce specific genetic changes in target DNA sequences in prokaryotic and eukaryotic cells or episomes thereof. Such changes can be used to create new phenotypic traits not found in nature, in a subject as a therapeutic or prophylactic intervention and as an investigational tool.

6. DETAILED DESCRIPTION OF THE INVENTION 6.1. The Generic Structure Of The Chimetric Mutational Vector The Duplex Mutational Vectors (DMV) are comprised of polymers of nucleobases, which polymers hybridize, i.e., form Watson-Crick base pairs of purines and pyrimidines, to DNA having the appropriate sequence. Each DMV is divided into a first and a second strand of at least 12 nucleobases and not more than 75 nucleobases. In a preferred embodiment the length of the strands are each between 20 and 50 nucleobases. The strands contain regions that are complementary to each other. In a preferred embodiment the two strands are complementary to each other at every nucleobase except the nucleobases wherein the target sequence and the desired sequence differ. At least two non-overlapping regions of at least 5 nucleobases are preferred.

Nucleobases contain a base, which is either a purine or a pyrimidine or analog or derivative thereof. There are two types of nucleobases. Ribo-type nucleobases are ribonucleosides having a 2'-hydroxyl, substituted 2'-hydroxyl or 2'-halo-substituted ribose. All nucleobases other than ribo-type nucleobases are deoxyribo-type nucleobases. Thus, deoxy-type nucleobases include peptide nucleobases.

In the embodiments wherein the strands are complementary to each other at every nucleobase, the sequence of the first and second strands consists of at least two regions that are homologous to the target gene and one or more regions (the "mutator regions") that differ from the target gene and introduce the genetic change into the target gene. The mutator region is directly adjacent to homologous regions in both the 3' and 5' directions. In certain embodiments of the invention, the two homologous regions are at least three nucleobases, or at least six nucleobases or at least twelve nucleobases in length. The total length of all homologous regions is preferably at least 12 nucleobases and is preferably 16 and more preferably 20 nucleobases to about 60 nucleobases in length. Yet more preferably the total length of the homology and mutator regions together is between 25 and 45 nucleobases and most preferably between 30 and 45 nucleobases or about 35 to 40 nucleobases. Each homologous region can be between 8 and 30 nucleobases and more preferably be between 8 and 15 nucleobases and most preferably be 12 nucleobases long.

One or both strands of the DMV can optionally contain ribo-type nucleobases. In a preferred embodiment a first strand of the DMV consists of ribo-type nucleobases only while the second strand consists of deoxyribo-type nucleobases. In an alternative embodiment the first strand consists of a single segment of deoxyribo-type nucleobases interposed between two segments of ribo-type nucleobases. In said alternative embodiment the interposed segment contains the mutator region or, in the case of a HDMV, the intervening region is paired with the mutator region of the alternative strand.

Preferably the mutator region consists of 20 or fewer bases, more preferably 6 or fewer bases and most preferably 3 or fewer bases. The mutator region can be of a length different than the length of the sequence that separates the regions of the target gene homology with the homologous regions of the DMV so that an insertion or deletion of the target gene results.

When the DMV is used to introduce a deletion in the target gene there is no base identifiable as within the mutator region. Rather, the mutation is effected by the juxtaposition of the two homologous regions that are separated in the target gene. For the purposes of the invention, the length of the mutator region of a DMV that introduces a deletion in the target gene is deemed to be the length of the deletion. In one embodiment the mutator region is a deletion of from 6 to 1 bases or more preferably from 3 to 1 bases. Multiple separated mutations can be introduced by a single DMV, in which case there are multiple mutator regions in the same DMV. Alternatively multiple DMV can be used simultaneously to introduce multiple genetic changes in a single gene or, alternatively to introduce genetic changes in multiple genes of the same cell. Herein the mutator region is also termed the heterologous region. When the different desired sequence is an insertion or deletion, the sequence of both strands have the sequence of the different desired sequence.

The DMV is a single oligonucleobase compound (polymer) of between 24 and 150 nucleobases. Accordingly the DMV contains a single 3' end and a single 5' end. The first and the second strands can be linked covalently by nucleobases or by non-oligonucleobase linkers. As used herein such linkers are not regarded as a part of the strands. Accordingly, a limitation, for example that a strand contain no ribo-type nucleobases does not exclude ribo-type nucleobases from a linker attached to said strand. As used herein, Chimeric, Non-Chimeric and Heteroduplex Mutational Vectors are each types of DMV and have the above properties.

In a preferred embodiment the 3' terminal nucleobase of each strand is protected from 3' exonuclease attack. Such protection can be achieved by several techniques now known to these skilled in the art or by any technique to be developed. In one embodiment protection from 3'-exonuclease attack is achieved by linking the 3' most (terminal) nucleobase of one strand with the 5' most (terminal) nucleobase of the alternative strand by a nuclease resistant covalent linker, such as polyethylene glycol, poly-1,3 -propanediol or poly-1,4-butanediol. The length of various linkers suitable for connecting two hybridized nucleic acid strands is understood by those skilled in the art. A polyethylene glycol linker having from six to three ethylene units and terminal phosphoryl moieties is suitable. Durand, M. et al., 1990, Nucleic Acid Research 18, 6353; Ma, M. Y-X., et al., 1993, Nucleic Acids Res. 21, 2585–2589. A preferred alternative linker is bis-phosphorylpropyl-trans-4, 4'-stilbenedicarboxamide. Letsinger, R. L., et alia, 1994, J. Am. Chem. Soc. 116, 811–812; Letsinger, R. L. et alia, 1995, J. Am. Chem. Soc. 117, 7323–7328, which are hereby incorporated by reference. Such linkers can be inserted into the DMV using conventional solid phase synthesis. Alternatively, the strands of the DMV can be separately synthesized and then hybridized and the interstrand linkage formed using a thiophoryl-containing stilbenedicarboxamide as described in patent publication WO 97/05284, Feb. 13, 1997, to Letsinger R. L. et alia.

In a further alternative embodiment the linker can be a single strand oligonucleobase comprised of nuclease resistant nucleobases, e.g., a 2'-O-methyl, 2'-O-allyl or 2'-F-ribonucleotides. The tetranucleotide sequences TTTT, UUUU and UUCG and the trinucleotide sequences TTT, UUU, or UCG are particularly preferred nucleotide linkers. A linker comprising a tri or tetrathymidine oligonucleotide is not comprised of nuclease resistant nucleobases and such linker does not provide protection from 3' exonuclease attack.

In an alternative embodiment, 3'-exonuclease protection can be achieved by the modification of the 3' terminal nucleobase. If the 3' terminal nucleobase of a strand is a 3' end, then a steric protecing group can be attached by esterification to the 3'-OH, the 2'-OH or to a 2' or 3' phosphate. A suitable protecting group is a 1,2-(ω-amino)-alkyldiol or alternatively a 1,2-hydroxymethyl-(ω-amino)-alkyl. Modifications that can be made include use of an alkene or branched alkane or alkene, and substitution of the ω-amino or replacement of the ω-amino with an ω-hydroxyl. Other suitable protecting groups include a 3' end methylphosphonate, Tidd, D. M., et alia, 1989, Br. J. Cancer, 60, 343–350; and 3'-aminohexyl, Gamper H. G., et al., 1993, Nucleic Acids Res., 21, 145–150. Alternatively, the 3' or 5' end hydroxyls can be derivatized by conjugation with a substituted phosphorus, e.g., a methylphosphonate or phosphorothioate.

In a yet further alternative embodiment the protection of the 3'-terminal nucleobase can be achieved by making the 3'-most nucleobases of the strand nuclease resistant nucleobases. Nuclease resistant nucleobases include peptide nucleic acid nucleobases and 2' substituted ribonucleotides. Suitable substituents include the substituents taught by U.S. Pat. No. 5,731,181, and by U.S. Pat. Nos. 5,334,711 and 5,658,731 to (Sproat), which are hereby incorporated by reference, and the substituents taught by patent publications EP 629 387 and EP 679 657 (collectively, the Martin Applications), which are hereby incorporated by reference. As used herein a 2' fluoro, chloro or bromo derivative of a ribonucleotide or a ribonucleotide having a substituted 2'-O as described in the Martin Applications or Sproat is termed a "2'-Substituted Ribonucleotide." Particular preferred embodiments of 2'-Substituted Ribonucleotides are 2'-fluoro, 2'-methoxy, 2'-propyloxy, 2'-allyloxy 2'-hydroxylethyloxy, 2'-methoxyethyloxy, 2'-fluoropropyloxy and 2'-trifluoropropyloxy substituted ribonucleotides. In more preferred embodiments of 2'-Substituted Ribonucleotides are 2'-fluoro, 2'-methoxy, 2'-methoxyethyloxy, and 2'-allyloxy substituted nucleotides.

The term "nuclease resistant ribonucleoside" encompasses including 2'-Substituted Ribonucleotides and also all 2'-hydroxyl ribonucleosides other than ribonucleotides, e.g., ribonucleotides linked by non-phosphate or by substituted phosphodiesters. Nucleobase resistant deoxyribonucleosides are defined analogously. In a preferred embodiment, the DMV preferably includes at least three and more preferably six nuclease resistant ribonucleosides. In one preferred embodiment the CMV contains only nuclease resistant ribonucleosides and deoxyribonucleotides. In an alternative preferred embodiment, every other ribonucleoside is nuclease resistant.

Each DMV has a single 3' end and a single 5' end. In one embodiment the ends are the terminal nucleobases of a strand. In an alternative embodiment a strand is divided into two chains that are linked covalently through the alternative strand but not directly to each other. In embodiments wherein a strand is divided into two chains the 3' and 5' ends are Watson-Crick base paired to adjacent nucleobases of the alternative strand. In such strands the 3' and 5' ends are not terminal nucleobases. A 3' end or 5' end that is not the terminal nucleobase of a strand can be optionally substituted with a steric protector from nuclease activity as described above. In yet an alternative embodiment a terminal nucleobase of a strand is attached to an nucleobase that is not paired to a corresponding nucleobase of the opposite strand and is not a part of an interstrand linker. Such embodiment has a single "hairpin" conformation with a 3' or 5' "overhang." The unpaired nucleobase and other components of the overhang are not regarded as a part of a strand. The overhang may include self-hybridized nucleobases or non-nucleobase moieties, e.g., affinity ligands or labels. In a particular preferred embodiment of DMV having a 3' overhang, the strand containing the 5' nucleobase is composed of deoxy-type nucleobases only, which are paired with ribo-type nucleobase of the opposite strand. In a yet further preferred embodiment of DMV having a 3' overhang, the sequence of the strand containing the 5' end nucleobase is the different, desired sequence and the sequence of the strand having the overhang is the sequence of the target DNA.

A particularly preferred embodiment of the invention is a DMV wherein the two strands are not fully complementary. Rather the sequence of one strand comprises the sequence of the target DNA to be modified and the sequence of the alternative strand comprises the different, desired sequence that the user intends to introduce in place of the target sequence. It follows that at the nucleobases where the target and desired sequences differ, the bases of one strand are paired with non-complementary bases in the other strand. Such DMV are termed herein Heteroduplex Mutational Vectors (HDMV). In one preferred embodiment, the desired sequence is the sequence of a chain of a divided strand. In a second preferred embodiment, the desired sequence is found on a chain or a strand that contains no ribo-type nucleobases. In a more preferred embodiment, the desired sequence is the sequence of a chain of a divided strand, which chain contains no ribo-type nucleobases.

In yet a second particularly preferred embodiment, the first strand of the CMV does not contain an intervening segment of deoxy-type nucleobases between two segments of ribo-type nucleobases. In such embodiment, the second strand is divided into a first chain and a second chain, which first chain is comprised of no ribo-type nucleobases and the portion of the first strand paired therewith contains fewer than four and preferably no deoxyribotype nucleobases. In a preferred embodiment the first chain contains the 5' end nucleobase. A yet further preferred embodiment is a Heteroduplex Mutational Vector having a single ribo-type segment according to the above, wherein the sequence of the ribo-type segment is the target DNA sequence and the sequence of the different, desired sequence is the sequence of the first chain.

6.2. Internucleobase Linkages

The linkage between the nucleobases of the strands of a DMV can be any linkage that is compatible with the hybridization of the DMV to its target sequence. Such sequences include the conventional phosphodiester linkages found in natural nucleic acids. The organic solid phase synthesis of oligonucleotides having such nucleotides is described in U.S. Pat. No. Re: 34,069.

Alternatively, the internucleobase linkages can be substituted phosphodiesters, e.g., phosphorothioates, substituted phosphotriesters. Alternatively, non-phosphate, phosphorus-containing linkages can be used. U.S. Pat. No. 5,476,925 to Letsinger describes phosphoramidate linkages. The 3'-phosphoramidate linkage (3'-NP(O$^-$)(O)O-5') is well suited for use in DMV because it stabilizes hybridization compared to a 5'-phosphoramidate. Non-phosphate linkages between nucleobases can also be used. U.S. Pat. No. 5,489,677 describes internucleobase linkages having adjacent N and O and methods of their synthesis. The linkage 3'-ON (CH$_3$)CH$_2$-5' (methylenemethylimmino) is a preferred embodiment. Other linkages suitable for use in DMV are described in U.S. Pat. No. 5,731,181 to Kmiec. Nucleobases that lack a pentosefuranosyl moiety and are linked by peptide bonds can also be used in the invention. Oligonucleobases containing such so-called peptide nucleic acids (PNA) are described in U.S. Pat. No. 5,539,082 to Nielsen. Methods for making PNA/nucleotide chimera are described in WO 95/14706.

An complete review of the modifications at the 2' position and of the internucleobase linkage is found in Freier, S. M., & Altmann, K-H., 1997, Nucleic Acids Research 25, 4429–4443.

6.3. Uses of Duplex Mutational Vectors

Duplex Mutational Vectors (DMV) and particularly Non-Chimeric Mutational Vectors can be used to introduce changes into a target DNA sequence of a cell. DMV can be used according to the teaching and for the purposes that have been described by Chimeric Mutational Vectors. See, e.g., WO 97/41141 to Kmiec and Kren, B. T., et al., 1998, Nature Medicine 4, 285–290.

The invention further encompasses the use of Duplex Mutational Vectors including Chimeric Mutational Vectors in prokaryotic cells that are transformation and recombination/repair competent. Mutational Vectors can be used to make specific changes in a DNA sequence of a plasmid within a bacteria, of a bacterial gene or of a bacterial artificial chromosome (BAC). Bacterial Artificial Chromosomes have been constructed based on either the bacterial F-factor origin of replication, Shizuya, H., et al., 1992, Nature Genetics 6. 8794–8797; Hosoda, F., et al., 1990, Nucleic Acids Research 18, 3863–3869, or on the P-1 plasmid origin of replication, Ioannou, P. A., et al., 1994, Nature Genetics 6, 84–90. Heretofore the introduction of specific genetic changes in a BAC have required the construction of a plasmid containing the change followed by two recombinational events. Yang, X. W., et al., 1997, Nature Biotechnology 15, 859–865; Messerle, M., et al., 1997, Proc. Natl. Acad. Sci. 94, 14759–14763. The single copy PI based BAC pBeloBAC11, which is commercially available from Genome Systems, St. Louis Mo., is suitable for use in this embodiment of the invention.

Use of Mutational Vectors in bacteria requires that the bacteria have functional RecA and MutS genes. The RecA function can be constitutive or can be provided by a RecA gene operably linked to an induceable promoter such as the lac promoter, as shown in pAC184ΔTETRecA$^-$. When an induceable promoter is used, RecA need be induced only for about 1 hour prior to the cells being made transformation competent and then for about one hour after electroporation. The use of an induceable RecA is preferred for certain applications where a plasmid or a bacterial artificial chromosome may be genetically destabilized by the continuous presence of RecA. Those skilled in the art will appreciate that a dominant negative RecA mutation, such as found in DH5α is unsuitable for use in the invention. Unexpectedly, activity for Mutational Vectors cannot be restored by introduction of RecA mutants that are recombinase active but lack other functions, e.g., RecAPro67.

A Mutational Vector can be introduced into the bacteria by any means that can be used to transform bacteria with plasmid DNA. In one embodiment the chimera are introduced by electroporation. The cells can be made electroporation competent by the techniques used for plasmids. The competent bacteria are then suspended in sterile nanopure water with Mutational Vectors at a concentration of between 10 ng and 10 μg per $10^8$ bacteria. Electroporation is performed in a total volume of 40 μl.

In a preferred embodiment the DMV are introduced by electroporation into the bacteria. The DMV, at about 1–2 mg/ml, are preincubated with spermidine at between 3 nM and 200 nM at room temperature in a volume of 2–4 μl prior to mixing with the bacteria to a final volume of 40 μl and electroporated. Preferably the spermidine concentration is between 5 nM and 50 nM and most preferably is about 10 nM. Without limitation as to theory, such spermidine pre-incubation causes the DMV to adhere to the bacteria prior to electroporation, which is believed to cause an increased rate of directed mutation. In place of spermidine, spermine or an equivalent linear polyalkylamine can be used.

Table I below shows a comparison of the rates of directed mutation in bacteria and the rates that were obtained using a cell-free extract from HuH-7 hepatocarcinoma cell line. The extract-treated DMV are then electroporated into RecA defective bacteria and the numbers of kanamycin resistant colonies per ampicillin resistant colony calculated. The comparison shows there to be an excellent correlation between activity in the extract and activity in the bacterial system. In particular, in both systems variants IV and VIb are superior to Kany.y and in both systems Non-Chimeric Mutational Vectors having 3' exonuclease protected termini are active. The only disparity is variant VII, which contains solely deoxynucleotides. Variant VII is active in the cell-free extract but not the bacterial system. Deoxyoligonucleotides have also been found inactive in eukaryotic cells. Without limitation as to theory, applicants believe that the activity of variant VII in the cell-free system is due to the reduced amount of nucleases present in the system compared to cell-containing systems. Based on these results, bacterial chimeraplasty can be used to test variant structures of recombinagenic oligonucleobases for use in eukaryotic studies.

7. EXAMPLES
7.1. Materials and Methods

Construction of Plasmids: All DNA fragments and vectors used in cloning were isolated by gel electrophoresis and purified using the Geneclean II Kit (BIORAD101). PCR reactions were performed as follows 1–100 ng of target or genomic DNA, 5 μL 10X buffer with $Mg^{++}$ (Boehringer Manheim), 0.5 μl of 25 mM dNTPs, 2.5 Units of Taq DNA Polymerase (Boehringer Mannheim), 20 pmol of each primer were mixed in a 50 μL volume. The cycling program was: 94° C. for 5 minutes, followed by 30 cycles of 94° C. for 30 sec., 55° C. for 30 sec., 72° C. for 30 sec., followed by an extension at 72° C. for 7 minutes. To make pWE15Kan$^s$, a single T→G point mutation was introduced at nucleotide position 4021 of the pWE15 vector (Stratagene) which introduced a TAG termination codon and a new BfaI site within the kanamycin gene. The mutant kanamycin fragment was generated from pWE15 template using the following PCR primer sets: Set A=Kan3910 (5'CAGGGGATCA<u>AGATC</u>TGAT3' (SEQ ID No. 1)-underlined bases indicate BglII site) and Kan4010 (5'CCCAGTC<u>CTAG</u>CCGAATAG 3' (SEQ ID No. 2)) Set B=Kan4014 (5'TCGG<u>CTAG</u>GACTGGGCACA 3' (SEQ ID No. 3)-underlined bases indicate BfaI site and bold indicates the point mutation) and Kan4594 (5'TGATAG<u>CGGTCCG</u>CCACA 3' (SEQ ID No. 4)-underlined bases indicate RsrII site.) Following digestion of product A with BglII and product B with RsrII, both products were digested with BfaI and ligated together. The resultant mutant fragment was cloned into pWE15 linearized with BglII and RsrII, creating pWE15Kan$^s$. E. coli strains carrying pWE15Kan$^s$ plasmid are kanamycin sensitive.

The mutant pBR322 plasmid, pBRT$^s$Δ208, contains a base deletion at position 208, which results in early termination of the tetracycline gene. The deletion was created through an overlap PCR procedure as described above. The DNA products carrying the mutations were generated using primer set A {5BR22 (5'CATCGATAAGCTTTAATGC 3' (SEQ ID No. 5)) and (3BRSPH 5'CATAGTGACTGGCAT-GCTGTCGGA 3' (SEQ ID No. 6))} and primer set B {3BR496 (5'GCTCATGAGCCCGAAGTGGC3' (SEQ ID No. 7)) and (5BRSPH 5'TCCGACAGCATGCCAGTCAC-TATG 3' (SEQ ID No. 8))}. The two products were ligated together at the created SphI site. The resulting fragment was digested with HindIII and BamHI and was used to replace the analogous region in the wildtype pBR322 plasmid. The base deletion creates an SphI site at position 208. The mutant pBR322 plasmid, pBRT$^s$m153(G), contains a stop codon in the tetracycline gene at codon 6 and was created through an overlap Polymerase Chain Reaction (PCR) procedure using fragments mixed from PCR primer set A {(5BR22 (SEQ ID No. 5) and 3BRBfa (5'CGGCATAAC<u>CTAG</u>CCTATGCC3' (SEQ ID No. 9))] and primer set B [(3BR496 (SEQ ID No. 7)) and 5BRBfa (5'GG<u>CTAG</u>GTTATGCCGGTACTG3' (SEQ ID No. 10)}. The mixed products were re-amplified using primers 5BR22 and 3BR496. The resulting product was digested with HindIII and BamHI and was used to replace the analogous region in the wildtype pBR322 plasmid. The introduction of a G at position 153 creates a stop codon and introduces a BfaI digestion site. Additionally an A→FG silent mutation in the tetracycline gene at position 325 was created to enable the distinction of converted from wildtype pBR322. E. coli strains harboring pBRT$^s$Δ208 and pBRT$^s$m153(G) plasmids are tetracycline sensitive. pET21aT$^R$ was prepared by cloning the EcoRI and StyI fragments into similarly digested pET21 a(+) (Novagen) vector. pET21aT$^R$ was able to confer tetracycline resistance to E. coli strains. pET21aT$^s$Δ208 and pET21 aT$^s$m153 were prepared by replacing the HindIII and SalI region of pET21aT$^R$ was replaced with that of pBRT$^s$m 153(G) and pBRΔ208, respectively. E. coli carrying pET21aT$^s$m153(G) and pET21aT$^s$Δ208 were sensitive to tetracycline.

Construction of pAC184ΔTETRecA+: The tetracycline region of pACYC184 (New England Bio Labs) vector was removed by digestion with AvaI and XbaI and replaced by an AvaI and XbaI linker {(184delTet-1 (5'TCGGAGGATCCAATCTCGAGTGCACTGAAAC 3'(SEQ ID No. 11) annealed to 184delTet-2 (5'CTAGGTTTCAGTGCACTCGAGATTGGATCCT3' (SEQ ID No. 12))} to make the intermediate cloning vector pAC 184ΔTET. pAC 184ΔTETRecA and pAC184ΔTETRecA$^m$ were prepared by cloning RecA or RecA$^m$ products in to the BclI site of pAC184ΔTET. RecA and RecA[m] inserts were prepared by PCR amplification of pUCRecA and pUCRecA[m] using primers 5RecALinkBClI (5'GCG<u>TGATCA</u>TGCACCATATGACGATTAAA3' (SEQ ID No. 13)) and 3RecALinkBcII (5'GCG<u>TGATCA</u>AGGAAGCGGAAGAGCGCCCA3' (SEQ ID No. 14)). The linkers define a region that contains the LacO, regulatory region (XXX) of pUC19, and the coding regions of wildtype RecA and RecA mutant (inframe deletion-removing amino acids X to X) respectively, inframe with the first five amino acids of the LacZ gene.

Construction of pAC184ΔTETRec variants: The sequence of the coding region for the RecA mutants was previously described (REF). pAC184ΔTETRec67, pAC 184ΔTETRec616 and pAC184ΔTETRec659 were made by four primer PCR reactions using primers (recAxba-rec67A, rec67B, recAndel, recA616A, recA616B, RecA659A, RecA659B). XbaI/NdeI fragments containing the specific mutations were cloned into the XbaI/NdeI cassette of the pAC184ΔTETRec. The positive clones were isolated and the sequence was confirmed.

Construction of pAC184ΔTETmutS: The MutS gene was amplified from genomic DNA isolated from E.coli DH5α by PCR using primers MutS5' XbaI (5'GCG<u>TCTAGA</u>GATGAGTGCAATAGAAAATTT3' (SEQ ID No. 15)) and MutS3' AseI (5'GCGA<u>TTAATT</u>TACACCAGACTCTTCAAGC3' (SEQ ID No. 16)). The MutS PCR product was purified using QIAquick PCR Purification Kit (Qiagen) and ligated into pGEMO®-T vector (Promega) for direct TA cloning of pGEMTmutS vector. The intact wildtype MutS coding region was confirmed by sequencing. The MutS XbaI and AseI insert was ligated to the XbaI and NdeI digested pAC 184ΔTetRecA expression vector, which replaces the RecA coding region with that of MutS.

Bacteria Strains and genotypes, media, and growth conditions: E. coli strains used in this study include RR1, MC1061, WM1100, BMS71-18, and EMSOmutS. Cells were grown in LB broth or on LB plates (10). Where appropriate cells were grown in the presence of the following antibiotics: kanamycin (50μg/mL), ampicillin, tetracycline, chloramphenicol. For transformation with plasmid or Chimera, cells were made electrocompetent essentially as described (11). Briefly, cells were grown in LB to an $OD_{600}$ of 0.5–0.7, concentrated by centrifugation (3000Xg for 10 minutes at 4° C.) to $\frac{1}{10}^{th}$ of the original volume, and washed several times (4–5) in ice-cold sterile nanopure $H_2O$. In the final wash, the bacteria pellet was resuspended in water (for immediate use) or 15% glycerol (for freezing at −80° C.) to $\frac{1}{500}^{th}$ of the original volume.

Electrocompetent cells were either frozen immediately or were placed on ice until electroporation (up to 24 hours).

Transfection of chimera: Electrocompetent E. coli strains MC 1061, WM100 and RR1 containing either pWEl15Kan[s] (for kanamycin gene targeted conversion), pET21aT[s]m153 (G) or pBR322T[s]Δ208 (for tetracycline gene targeted conversion) were transfected with 1–2 μg of chimeras Kany.y, Tetm153 or TETΔ208, respectively, using standard electroporation conditions, 2.5 kV, 25μF, 200 Ohms. Immediately following electroporation, cells were grown for 1 hour in the presence of 1 mL of SOC (12) at 37° C. with moderate shaking. We varied the time of incubation after transformation to allow sufficient time for gene targeted conversion to occur prior to antibiotic selection. Typically, following recovery in SOC medium, the entire culture was then transferred to 4 mL of LB broth containing 10μg/mL kanamycin (Sigma) for 90 min at 37° C. while shaking. 1 mL of this culture was then transferred to 4mL of LB broth containing 50 μg/mL kanamycin at 37° C. for 3 hr while shaking, after which an aliquot (100 μL) plated on LB agar containing 50 μg/mL kanamycin and incubated overnight at 37° C. For each bacterial strain and for each electroporation condition, kill curves were performed, as previously described.

Analysis of plasmid DNA.

Plasmid DNA isolated from kanamycin resistant colonies following chimera treatment were used to transform competent DH5a bacteria. The bacteria were grown on LB plates containing ampicillin for determining total bacteria and kanamycin or tetracycline for conversion selection. Typically, from a primary isolate 3–5 secondary isolates were isolated and analyzed by RFLP. The two populations of alleles were maintained after three replatings demonstrating that the colonies evolved from a single bacterium that contained a mixture of converted and mutant plasmids, which were subcloned and analyzed by sequence or restriction digestion.

7.2. RESULTS

The general structure of a Duplex Mutational Vector for the introduction of kanamycin resistance is given below. The intervening segment, 3' homology region, and 5' homology region are designated "I", "H-3'" and "H-5'", respectively. The interstrand linkers are designate "L". An optional chi site (5'-GCTGGTGG-3') and its complement are indicated as X and X' respectively. The 3' and 5' mutator region are single nucleotides indicated as $M^{3'}$ and $M^{5'}$, respectively. Variant I is similar to the Chimeric Mutational Vectors described in Cole-Strauss, 1996, Science 273, 1386, and Kren, 1998, Nature Medicine 4, 285–290. Variant I is referred to as Kany.y elsewhere in this specification. The symbol "—" for a feature of a variant indicates that the feature of the variant is the same as variant I.

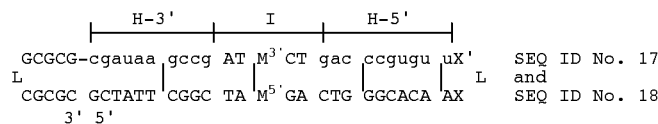

The above DMV causes a CG transversion that converts a TAG stop codon into a TAC tyr codon. Note that the first strand of I lacks an exonuclease protected 3' terminus and that the second strand of I is a divided strand, the first chain of which is the desired, different sequence. Variants IV and V are a Chimeric Mutational Vector and a Non-Chimeric Mutational Vector, respectively, having 3' termini exonuclease protected by a nuclease resistant linker (2'OMe-U$_4$). Variants VIa and VIb are Chimeric Heteroduplex Mutational Vectors. Variant VIb is the variant in which the desired, different sequence is found on the first chain, which chain consists of DNA-type nucleotides only.

The table below gives the activities of the variants relative to the variant I in a bacterial system and gives the frequency of conversion to kan$^r$/10$^5$ plasmids for a cell-free extract. The background rates were negligible compared to the experimental values except for variant VIa in the cell-free system and bacterial systems and variant VII in bacteria. The data reported for these variants are background corrected. Variants VIa and VII show low or absent activity. Each of variants III-V are superior in both systems to variant I, which is of the type described in the scientific publications of Yoon, Cole-Strauss and Kren cited herein above. Variant VIII is the optimal chimera based on inference from these data.

from these secondary transfectants were homogenous. Sequence of the plasmid of the secondary transfectants revealed the expected sequence in all cases except for variants VIa and VII.

The rate of conversion as a function of amount of recombinagenic oligonucleobase showed no maximum. Experiments using variant I at 0.01 µg/10$^8$ bacteria and 10, 100 and 1000 fold higher doses showed 5, 11, 56 and 320 converted colonies per 10$^5$ viable bacteria, post electroporation. The rates observed with TetΔ208T and Tet 153 were, respectively, about 10 fold and 2 fold lower than the rate observed with variant I at comparable concentrations.

The preincubation of variant I DMV with 10 nM spermidine resulted in an approximate eight fold further increase in the number of primary kanamycin resistant colonies. An increase was also seen at 100 nM spermidine, however, no increase was apparent at 1 nM, while 1.0 mM was inhibitory.

Variant II contains a bacterial chi site (5'GCTGGTG3') inserted between the H-5'and the linker as shown at X and

| DMV | M$^{5'}$ | M$^{3'}$ | H5' | I | H3' | L | X(X') | Rel. Act. bacteria | kan$^r$/ 10$^5$ amp$^r$ cell-free |
|---|---|---|---|---|---|---|---|---|---|
| I | C | G | 2'-OMe | DNA | 2'-OMe | T$_4$ | None | 1 | 6.0 |
| II | — | — | — | — | — | — | chi† | 3.2 | ≈1.5‡ |
| III | — | — | — | 2'-OMe | — | — | — | 1.6 | 13 |
| IV | — | — | — | — | — | 2'-OMe—U$_4$ | — | 10.0 | 50 |
| V | — | — | DNA | — | DNA | 2'-OMe—U$_4$ | — | 3.0 | 9.8 |
| VIa | G | — | — | — | — | — | — | 0.06* | 0.25 |
| VIb | — | C | — | — | — | — | — | 7.5 | 10.8 |
| VI | — | — | — | — | — | T$_3$ | — | 4.2 | N.D. |
| VII | — | — | DNA | — | DNA | — | — | ~0 | 4.4 |
| VIII | — | C | 2'-OMe | 2'-OMe | 2'-OMe | 2'-OMe—U$_4$ | — | N.D. | N.D. |

*Site Specific Rate
‡Result from an independent experiment normalized to other data
†GCTGGTGG The rate of mutation can be determined by comparison of the number of kanamycin resistant (mutated) and ampicillin resistant colonies. Variant IV results in the mutation of a plasmid in between 1% and 2% of the viable bacteria, post electroporation, when used at between 1 µg and 2 µg of mutational vector per 10$^8$ cells without the addition of spermidine on the strain MC1061. The absolute rate of mutation cannot be determined because each bacteria contains multiple copies of the pWEKan$^s$ plasmid. For each variant, plasmid preparations were made from selected kanamycin resistant colonies, bacteria transformed and selected for kanamycin resistance. Plasmid preparations X'. The replacement of the 3' most nucleotides (5'CGCGC3') by the chi site resulted in a Mutational Vector having less than a third of the activity of variant I.

Two tetracycline specific DMV were constructed and tested. TetΔ208T causes the insertion of a T that corrects a frameshift mutation. Tet 153 causes an AT transversion that converts a TAG stop codon to a TTG leu codon. The structure of tetracycline resistance Chimeric Mutational Vectors are given below

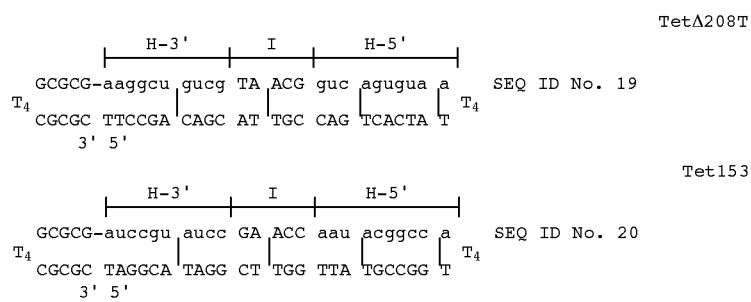

We claim:

1. A heteroduplex mutational vector comprising:
   (a) a first oligonucleobase strand of at least 12 linked nucleobases and not more than 75 linked nucleobases, which first oligonucleobase strand has a first and a second terminal nucleobase;
   (b) a second oligonucleobase strand having a 3' most and a 5' most nucleobase and having a number of nucleobases equal to the first oligonucleobase strand, which second oligonucleobase strand is optionally divided into a first chain and a second chain; and
   (c) a single 3' end nucleobase and a single 5' end nucleobase;
in which
   (i) the 3' most and 5' most nucleobases of the second oligonucleobase strand are Watson-Crick base paired to the first terminal and the second terminal nucleobase of the first oligonucleobase strand, respectively,
   (ii) the 3' most nucleobase of the second oligonucleobase strand and the second terminal nucleobase of the first oligonucleobase strand are protected from 3' exonuclease attack, and
   (iii) the second oligonucleobase strand contains at least two non-overlapping regions of at least 5 contiguous nucleobases that are Watson-Crick base paired to nucleobases of the first oligonucleobase strand,
provided that at least one nucleobase of the first oligonucleobase strand is paired with a non-complementary base of the second oligonucleobase strand.

2. The vector of claim 1, in which the first oligonucleobase strand comprises not more than 50 nucleobases.

3. The vector of claim 1, in which not more than 3 nucleobases of the first oligonucleobase strand are paired with non-complementary nucleobases of the second oligonucleobase strand.

4. The vector of claim 3, in which the non-complementary nucleobases are deoxyribo-type nucleobases.

5. The vector of claim 3, in which not more than one nucleobase of the first oligonucleobase strand is paired with a non-complementary nucleobase of the second oligonucleobase strand.

6. The vector of claim 3, in which the second oligonucleobase strand is comprised of a first chain and a second chain and the first chain contains a mismatched nucleobase.

7. The vector of claim 6, in which the first chain contains no ribo-type nucleobases.

8. The vector of claim 6, in which the first chain contains the 5' end nucleobase.

9. The vector of claim 3, in which the first oligonucleobase strand contains at least 10 ribo-type oligonucleobases.

10. The vector of claim 9, in which the first oligonucleobase strand contains no deoxyribo-type oligonucleobases.

11. The vector of claim 1, in which the 5' most nucleobase is linked by a nuclease resistant linker to the second terminal nucleobase, whereby said second terminal nucleobase is protected from 3' exonuclease attack.

12. The vector of claim 1, in which the 3' most nucleobase is linked by a nuclease resistant linker to the first terminal nucleobase, whereby said 3' most nucleobase is protected from 3' exonuclease attack.

13. The vector of claim 12, in which the 5' most nucleobase is linked by a nuclease resistant linker to the second terminal nucleobase, whereby said second terminal nucleobase is protected from 3' exonuclease attack.

14. The vector of claim 12, in which the linker comprises a moiety selected from the group consisting of 2'-methoxy-uridine, 2'-allyloxy-uridine, 2'-fluoro-uridine, 2'-methoxy-thymidine, 2'-allyloxy-thymidine, 2'-fluoro-thymidine, polyethylene glycol and trans-4,4'-stilbenecarboxamide.

15. The vector of claim 1, in which the first chain contains no ribo-type nucleobases.

16. The vector of claim 1, in which the 3' end nucleobase is protected from 3' exonuclease activity by a blocking group.

17. A chimeric duplex mutational vector having no intervening segment comprising:
   (a) a first oligonucleobase strand of at least 12 linked nucleobases and not more than 75 linked nucleobases, which first oligonucleobase strand has a first terminal and a second terminal nucleobase;
   (b) a second oligonucleobase strand having a 3' most nucleobase and a 5' most nucleobase and having a number of nucleobases equal to the first strand, which second oligonucleobase strand is divided into a first chain and a second chain; and
   (c) a 3' end nucleobase and a 5' end nucleobase;
in which
   (i) the 3' most and 5' most nucleobases of the second oligonucleobase strand are Watson-Crick base paired to the first terminal and the second terminal nucleobase of the first oligonucleobase strand, respectively,
   (ii) the nucleobases of the first chain are deoxy-type nucleobases and nucleobases of the first oligonucleobase strand paired therewith are nuclease resistant ribo-type nucleobases,
   (iii) the second oligonucleobase strand contains at least two non-overlapping regions of at least 5 contiguous nucleobases that are Watson-Crick base paired to nucleobases of the first oligonucleobase strand,
provided that the first oligonucleobase strand does not contain an intervening segment of deoxy-type nucleobases between two segments of ribo-type nucleobases.

18. The vector of claim 17, in which the first chain comprises the 5' end nucleobase.

19. The vector of claim 18, in which not more than one nucleobase of the first chain is paired with a non-complementary nucleobase of the first oligonucleobase strand.

20. The vector of claim 17, in which the 3' most nucleobase and the first terminal nucleobase are linked by a linker comprising a moiety selected from the group consisting of 2'-methoxy-uridine, 2'-allyloxy-uridine, 2'-fluoro-uridine, 2'-methoxy-thymidine, 2'-allyloxy-thymidine, 2'-fluoro-thymidine, polyethylene glycol and trans-4,4'-stilbenecarboxamide.

21. The vector of claim 17, in which the 5' most nucleobase and the second terminal nucleobase are linked by a linker comprising a moiety selected from the group consisting of 2'-methoxy-uridine, 2'-allyloxy-uridine, 2'-fluoro-uridine, 2'-methoxy-thymidine, 2'-allyloxy-thymidine, 2'-fluoro-thymidine, polyethylene glycol and trans-4,4'-stilbenecarboxamide.

22. An overhang containing chimeric duplex mutational vector having no intervening segment comprising:
   (a) an oligonucleobase strand of at least 12 linked nucleobases and not more than 75 linked nucleobases, which oligonucleobase strand has a first terminal and a second terminal nucleobase; and
   (b) an oligonucleobase chain having a 3' most nucleobase and a 5' end nucleobase; and (c) a 3' overhang attached to the second terminal nucleobase;

in which
  (i) the 3' most and 5' end nucleobases of the oligonucleobase chain are Watson-Crick base paired to the first terminal and the second terminal nucleobase of the oligonucleobase strand, respectively,
  (ii) the nucleobases of the oligonucleobase chain are deoxy-type nucleobases and nucleobases of the oligonucleobase strand paired therewith are nuclease resistant ribo-type nucleobases;
  (iii) the oligonucleobase chain contains at least two non-overlapping regions of at least 5 contiguous nucleobases that are Watson-Crick base paired to nucleobases of the oligonucleobase strand.

23. The vector of claim 22, in which at least one nucleobase of the oligonucleobase chain is paired with a non-complementary nucleobase of the oligonucleobase strand.

24. The vector of claim 23, in which not more than one nucleobase of the oligonucleobase chain is paired with a non-complementary nucleobase of the oligonucleobase strand.

25. The vector of claim 22, in which the 3' most nucleobase and the first terminal nucleobase are linked by a linker comprising a moiety selected from the group consisting of 2'-methoxy-uridine, 2'-allyloxy-uridine, 2'-fluoro-uridine, 2'-methoxy-thymidine, 2'-allyloxy-thymidine, 2'-fluoro-thymidine, polyethylene glycol and trans-4,4'-stilbenecarboxamide.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:1:

CAGGGGATCA AGATCTGAT                                               19

(2) INFORMATION FOR SEQ ID NO:2:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:2:

CCCAGTCCTA GCCGAATAG                                               19

(2) INFORMATION FOR SEQ ID NO:3:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:3:

TCGGCTAGGA CTGGGCACA                                               19

(2) INFORMATION FOR SEQ ID NO:4:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:4:

TGATAGCGGT CCGCCACA                                                18

(2) INFORMATION FOR SEQ ID NO:5:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:5:

CATCGATAAG CTTTAATGC												19

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:6:

CATAGTGACT GGCATGCTGT CGGA												24

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

GCTCATGAGC CCGAAGTGGC												20

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

TCCGACAGCA TGCCAGTCAC TATG												24

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

CGGCATAACC TAGCCTATGC C												21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

GGCTAGGTTA TGCCGGTACT G												21

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

TCGGAGGATC CAATCTCGAG TGCACTGAAA C                                    31

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:12:

CTAGGTTTCA GTGCACTCGA GATTGGATCC T                                    31

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:13:

GCGTGATCAT GCACCATATG ACGATTAAA                                       29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:14:

GCGTGATCAA GGAAGCGGAA GAGCGCCCA                                       29

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:15:

GCGTCTAGAG ATGAGTGCAA TAGAAAATTT                                      30

(2) INFORMATION FOR SEQ ID NO:16:

(i) SEQUENCE CHARACTERISTICS:
        (A) LENGTH: 29 base pairs

```
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:16:

GCGATTAATT TACACCAGAC TCTTCAAGC                                          29

(2) INFORMATION FOR SEQ ID NO:17:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:17:

GCTATTCGGC TASGACTGGG CACAAGCTGG TGGTTTTCCA CCAGCTTGTG CCCAGTCSTA        60

GCCGAATAGC GCGCGTTTTC GCGC                                               84

(2) INFORMATION FOR SEQ ID NO:18:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:18:

GCTATTCGGC TASGACTGGG CACAATTTTT TGTGCCCAGT CSTAGCCGAA TAGCGCGCGT        60

TTTCGCGC                                                                 68

(2) INFORMATION FOR SEQ ID NO:19:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:19:

TTCCGACAGC ATTGCCAGTC ACTATTTTTA TAGTGACTGG CAATGCTGTC GGAAGCGCGT        60

TTTCGCGC                                                                 68

(2) INFORMATION FOR SEQ ID NO:20:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:20:

TAGGCATAGG CTTGGTTATG CCGGTTTTTA CCGGCATAAC CAAGCCTATG CCTAGCGCGT        60

TTTCGCGC                                                                 68
```